United States Patent [19]

Leppard

[11] Patent Number: 5,298,380
[45] Date of Patent: Mar. 29, 1994

[54] PHOTOGRAPHIC MATERIAL WHICH CONTAINS A UV ABSOBER

[75] Inventor: David G. Leppard, Marly, Switzerland

[73] Assignee: Ciba-Geigy Corporation, Ardsley, N.Y.

[21] Appl. No.: 939,289

[22] Filed: Sep. 1, 1992

[30] Foreign Application Priority Data

Sep. 5, 1991 [CH] Switzerland ............... 2606/91-5

[51] Int. Cl.$^5$ ............................................ G03C 1/815
[52] U.S. Cl. .................................. 430/512; 430/931; 252/589; 548/261
[58] Field of Search ............... 430/512, 931; 252/589; 548/261

[56] References Cited

U.S. PATENT DOCUMENTS

| | | | |
|---|---|---|---|
| 3,738,837 | 6/1973 | Kuwabara et al. | 430/517 |
| 4,200,464 | 4/1980 | Shishido et al. | 430/512 |
| 4,220,711 | 9/1980 | Nakamura et al. | 430/512 |
| 4,946,768 | 8/1990 | Vallarino | 430/512 |
| 4,996,326 | 2/1991 | Leppard et al. | 548/261 |
| 5,047,314 | 9/1991 | Sakai et al. | 430/512 |

FOREIGN PATENT DOCUMENTS 0243199 10/1987 European Pat. Off. ............ 430/512
0323853 7/1989 European Pat. Off. .

OTHER PUBLICATIONS

Abstract of Japanese Patent J6 2118-344A, Nov. 1985, Konishiroku Photo KK (Corresponds to Applicants Ref. AS).
C.A. 107: 225909f, 1987.
Abst. 87-188723/27.

*Primary Examiner*—Charles L. Bowers, Jr.
*Assistant Examiner*—Thomas R. Neville
*Attorney, Agent, or Firm*—Luther A. R. Hall

[57] ABSTRACT

Compounds of formula

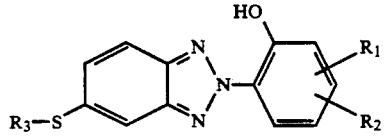

wherein $R_1$ is hydrogen, alkyl, phenylalkyl or cyclohexyl, $R_2$ is alkyl, phenylalkyl, cyclohexyl, alkoxy or hydroxyalkoxy, and $R_3$ is phenyl or substituted phenyl, are very suitable for use as UV absorbers in photographic materials with transparent substrates.

11 Claims, No Drawings

PHOTOGRAPHIC MATERIAL WHICH CONTAINS A UV ABSOBER

The present invention relates to a novel photographic film material which contains a UV absorber.

It is taught, inter alia, in U.S. Pat. Nos. 4,220,711, 4,200,464, 4,946,768 and EP-A-323 853 that UV light can have a harmful effect on photographic materials. Even during the production of such materials, discharges on the electrostatically charging transparent photographic substrates can result in exposure of the light-sensitive layers and appear as static marks in the developed image. Furthermore, when undeveloped photographic materials are exposed there is also the possibility that UV light will penetrate the materials, thereby giving rise to changes of colour, changes in gradation and, in particular, fogging in the developed image. These phenomena typically occur when photographing snowscapes, but they are also observed when using artificial light sources, such as tungsten lamps.

It is known to avoid such drawbacks by using UV absorbers. A special class of UV absorbers has now been found which is admirably suitable for this purpose.

Specifically, the present invention relates to photographic film material containing on a transparent substrate at least one silver halide emulsion layer and at least one light-insensitive layer, which material contains as UV absorber a compound of formula

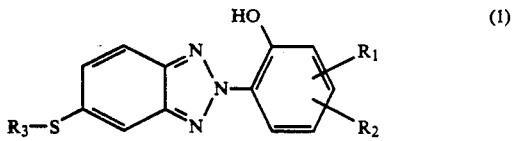

wherein $R_1$ is hydrogen, alkyl of 1 to 18 carbon atoms, phenylalkyl containing 1 to 4 carbon atoms in the alkyl moiety, cyclopentyl or cyclohexyl, $R_2$ is alkyl of 1 to 18 carbon atoms, phenylalkyl containing 1 to 4 carbon atoms in the alkyl moiety, cyclopentyl or cyclohexyl, hydroxyl or -$OR_4$, wherein $R_4$ is alkyl of 1 to 18 carbon atoms, hydroxyalkyl of 1 to 18 carbon atoms, or hydroxyalkyl of 4 to 18 carbon atoms which is interrupted by oxygen, or $R_2$ is —$CH_2CH_2COR_5$, wherein $R_5$ is —$OR_6$ or —$NR_7R_8$, wherein $R_6$ is hydrogen, alkyl of 1 to 18 carbon atoms, or hydroxyalkyl of 4 to 18 carbon atoms which is interrupted by oxygen, or is alkyl of 2 to 18 carbon atoms which is interrupted by oxygen and substituted by —$OR_9$, wherein $R_9$ is alkyl of 1 to 12 carbon atoms, or $R_6$ is alkenyl of 3 to 18 carbon atoms, and $R_7$ and $R_8$ are each independently of the other hydrogen or alkyl of 1 to 18 carbon atoms or, when taken together, are alkylene of 4 to 6 carbon atoms, 3-oxapentamethylene, 3-iminopentamethylene or 2-methyliminopentamethylene, and $R_3$ is alkyl of 6 to 18 carbon atoms, cyclopentyl, cyclohexyl, alkenyl of 3 to 18 carbon atoms, phenylalkyl containing 1 to 9 carbon atoms in the alkyl moiety, phenyl, phenyl which is substituted by one or two alkyl groups, each of 1 to 4 carbon atoms, or is a radical of formula

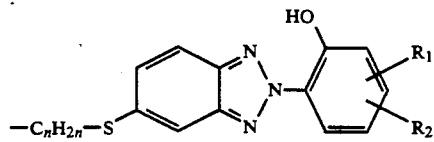

wherein n is 0 to 8, and $R_1$ and $R_2$ have the given meanings.

The compounds of formula (1) may contain alkyl radicals of up to 18 carbon atoms, typically methyl, ethyl, propyl, pentyl, hexyl, heptyl, octyl, t-octyl, nonyl, decyl, undecyl, dodecyl, tetradecyl and octadecyl as well as corresponding branched isomers. Alkenyl radicals containing up to 18 carbon atoms can be derived from the cite alkyl radicals. Alkenyl radicals useful in this invention may also be polyunsaturated. Suitable alkyl radicals which are interrupted by oxygen typically contain structural units such as —$CH_2CH_2$—$O_xCH_3$ and —$CH_2CH_2O_yCH_2CH_3$, where x and y are an integer from 1 to 8. Phenylalkyl radicals contain 1 to 9 carbon atoms in the alkyl moiety and are typically benzyl, phenylethyl, cumyl or phenylbutyl.

The compounds of formula (1) eligible for use in the practice of this invention have superior stability to UV radiation, heat and humidity. They can be incorporated in photographic layers without problems. Usually only a comparatively small amount of UV absorber is necessary for this purpose, as the compounds absorb UV light very effectively. Consequently the concentration of high-boiling organic solvent is also low, so that the increase in the thickness of the layers varies within acceptable limits. In addition, owing to their high absorption in the range from 300 to 400 nm, the compounds of formula (1) are especially suitable for preventing static marks. Furthermore, they are diffusion-resistant in the layers in which they are present and exert no harmful influence on the sensitometric properties of the film materials. However, the application of these very effective UV absorbers to film materials is limited. Because they have a yellowish intrinsic colour, they are not suitable for use as UV absorbers for photographic papers.

A particularly suitable photographic material for use in the practice of this invention is that containing a compound of formula (1), wherein $R_1$ is hydrogen, alkyl of 1 to 18 carbon atoms, cyclohexyl, benzyl or cumyl, $R_2$ is alkyl of 1 to 18 carbon atoms, cyclohexyl, benzyl, cumyl or —$CH_2CH_2CO_2R_6$, wherein $R_6$ has the given meaning, and $R_3$ is alkyl of 7 to 14 carbon atoms, phenyl or a radical of formula

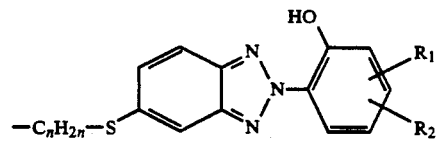

wherein n and $R_1$ and $R_2$ have the given meanings.

Preferred materials are those which contain a compound of formula (1), wherein $R_1$ is hydrogen, alkyl of 1 to 8 carbon atoms or cumyl, $R_2$ is alkyl of 1 to 8 carbon atoms, cumyl or —$CH_2CH_2CO_2R_6$, wherein $R_6$ is alkyl of 6 to 12 carbon atoms, and $R_3$ is alkyl of 7 to 14 carbon atoms or phenyl and, more particularly, those wherein $R_1$ is hydrogen or tert-butyl, $R_2$ is methyl, tert-butyl, —CH$_2$CH$_2$CO$_2$C$_8$H$_{17}$ or —CH$_2$CH$_2$CO$_2$C*$_8$H$_{17}$ (C*$_8$H$_{17}$: mixture of octyl isomers) and R$_3$ is phenyl.

The UV absorbers of formula (1) are preferably present in the substrate or in a layer above and/or below the substrate. In this case the inventive film materials are particularly well protected against static marks.

The compounds of formula (1) may also with advantage be present in light-sensitive and/or light-insensitive layers of the novel film materials. Materials which are stabilised in this manner are substantially protected against changes of colour, changes of gradation and, in particular, fogging. Typical light-insensitive layers are in particular interlayers, filter layers and protective layers.

The UV absorbers of formula (1) can be incorporated in the novel film materials by conventional known methods.

For example, the UV absorber is dissolved in a highboiling solvent, conveniently a higher alkyl- or arylphosphate, and the solution is emulsified together with an aqueous solution of a customary binder, typically gelatin or polyvinyl alcohol, in a colloid mill. In this procedure, auxiliaries such as additional solvents and stabilisers which prevent coagulation or crystallisation of the UV absorber may be used. Illustrative examples of such binders and auxiliaries are described in RESEARCH DISCLOSURE, November 1989, pages 873 to 876.

The appropriate layer of the film material will preferably contain the compounds of formula (1) in a casting weight of 5 to 1500 mg/m$^2$, preferably of 5 to 700 mg/m$^2$. Suitable substrates are the customary materials such as cellulose derivatives (nitrates, esters such as tri- and diacetate), polyamides, PVC copolymers, polycarbonates and the like. Such substrates are described on page 879 of the RESEARCH DISCLOSURE referred to above.

If it is desired to incorporate the UV absorbers of formula (1) in the substrate, these compounds can be dissolved in the casting solution which is used for the production of the substrates. This is especially the case if cellulose derivatives are chosen as substrates. If other substrates are used, e.g. polycarbonate, the UV absorbers are added to the casting melt.

The UV absorbers of formula (1) can also be used in conjunction with other types of UV absorbers such as 2-hydroxyphenyltriazines, 2-hydroxybenzophenones and/or oxanilides. Such compounds are disclosed, inter alia, in EP-A-0 453 396.

The novel film materials can contain the known types of silver halides. A detailed compilation of such silver halides will be found on pages 863–865 of the cited RESEARCH DISCLOSURE.

The novel film materials comprise black-white as well as colour materials, i.e. materials for chromogenic development, silver bleach materials, colour bleach materials and colour diffusion materials. Dye couplers suitable for chromogenic materials are listed in Chapters C, D, F and G on pages 871 to 872 of the cited RESEARCH DISCLOSURE.

A further object of the invention is a process for the reduction of static marks during the production of a photographic film material, which comprises incorporating a UV absorber of formula (1) in the transparent substrate of said material or in a layer above and/or under the substrate.

A further object of the invention is a process for reducing fogging during the exposure of a photographic film material, which comprises incorporating a UV absorber of formula (1) in the silver halide emulsion layer or layers.

UV Absorbers of formula (1) can be prepared by reacting known hydroxyphenylbenzotriazoles of formula

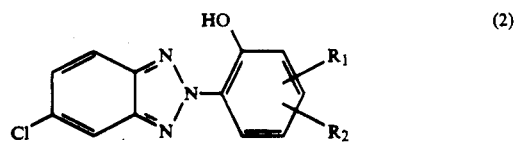

which are halogenated in 5-position, with the corresponding mercaptans of formula

R$_3$SH, (3)

wherein R$_1$, R$_2$ and R$_3$ have the given meanings.

The reaction is preferably carried out in an aprotic solvent such as N,N-dimethylformamide, N,N-dimethylacetamide, N-methylpyrrolidone or dimethyl sulfoxide in the temperature range from 30° to 200° C. The presence of a base which binds the hydrogen halide formed during the reaction is important. Suitable bases are typically carbonates and hydroxides of alkali metals and alkaline earth metals.

The invention is illustrated in more detail by the following Example, in which percentages are by weight.

EXAMPLE:

102 mg of UV absorber (q.v. Table) are dissolved in 2 ml of a solution of 2.4% of tricresyl phosphate in ethyl acetate. Then 1 ml of this solution is emulsified for 3 minutes by ultrasonication with 9 ml of an aqueous gelatin solution (containing 27.6 g/l of gelatin and 6.8 g/l of an 8% aqueous solution of 4,8-diisobutylnaphthyl-2-sodium sulfonate). To 7.5 ml of the emulsion so obtained are added 4.5 ml of a 0.24% aqueous solution of the sodium salt of 2-hydroxy-4,6-dichloro-1,3,5-triazine. Then 8 ml of this emulsion are applied as a layer to a polyester substrate (13×18 cm). The layer contains the UV absorber in a coating weight of 1.09 g/m$^2$. After a drying time of 7 days at room temperature, the UV absorption spectrum of the sample is recorded. The spectrum shows a broad absorption band (maximum at 377 nm) which extends into the yellow range.

TABLE

Structure (2):

$$\text{R}_3\text{-S-benzotriazole-N-phenyl(OH, R}_1\text{, R}_2\text{)}$$

| Compound | R₁ | R₂ | R₃ | m.p. (°C) |
|---|---|---|---|---|
| 100 | t-butyl | t-butyl | $C_{12}H_{25}$ | 64 |
| 101 | t-butyl | t-butyl | $C_6H_5$ | 134 |
| 102 | H | $CH_3$ | $C_6H_5$ | 111 |
| 103 | t-butyl | $CH_3$ | $CH_2C_6H_5$ | 141 |
| 104 | t-butyl | $CH_3$ | $C_6H_5$ | 133 |
| 105 | t-butyl | t-butyl | $C_8H_{17}$ | 81 |
| 106 | t-butyl | t-butyl | $C_{13}H_{27}$ | resin |
| 107 | t-butyl | t-butyl | —(CH₂)₆S— [benzotriazolyl-di-t-butylphenol] | 130 |
| 108 | t-butyl | t-butyl | [isoindolyl-di-t-butylphenol structure] | 265 |
| 109 | $C(CH_3)_2CH_2C(CH_3)_3$ | $C(CH_3)_2CH_2C(CH_3)_3$ | $C_6H_5$ | 86 |
| 110 | $C(CH_3)_2$—$C_6H_5$ | $C(CH_3)_2$—$C_6H_5$ | $C_6H_5$ | 120 |
| 111 | t-butyl | $CH_2CH_2CO_2C_8H_{17}$ | $C_6H_5$ | oil |
| 112 | t-butyl | $CH_2CH_2CO_2C^*_8H_{17}$ | $C_6H_5$ | oil |

$C^*_8H_{17}$: mixture of octyl isomers

What is claimed is:

1. Photographic film material containing on a transparent substrate at least one silver halide emulsion layer and at least one light-insensitive layer, which material contains as UV absorber a compound of formula

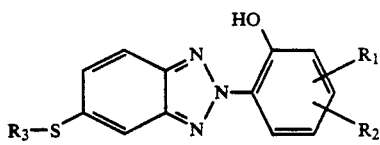

(1)

wherein $R_1$ is hydrogen, alkyl of 1 to 18 carbon atoms, phenylalkyl containing 1 to 4 carbon atoms in the alkyl moiety, cyclopentyl or cyclohexyl, $R_2$ is alkyl of 1 to 18 carbon atoms, phenylalkyl containing 1 to 4 carbon atoms in the alkyl moiety, cyclopentyl or cyclohexyl, hydroxyl or —OR₄, wherein R₄ is alkyl of 1 to 18 carbon atoms, hydroxyalkyl of 1 to 18 carbon atoms, or hydroxyalkyl of 4 to 18 carbon atoms which is interrupted by oxygen, or $R_2$ is —CH₂CH₂COR₅, wherein $R_5$ is —OR₆ or —NR₇R₈, wherein $R_6$ is hydrogen, alkyl of 1 to 18 carbon atoms, hydroxyalkyl of 1 to 18 carbon atoms or hydroxyalkyl of 4 to 18 carbon atoms which is interrupted by oxygen, or is alkyl of 2 to 18 carbon atoms which is interrupted by oxygen and substituted by —OR₉, wherein $R_9$ is alkyl of 1 to 12 carbon atoms, or $R_6$ is alkenyl of 3 to 18 carbon atoms, and $R_7$ and $R_8$ are each independently of the other hydrogen or alkyl of 1 to 18 carbon atoms or, when taken together, are alkylene of 4 to 6 carbon atoms, 3-oxapentamethylene, 3-iminopentamethylene or 2-methyliminopentamethylene, and $R_3$ is phenyl, phenyl which is substituted by one or two alkyl groups, each of 1 to 4 carbon atoms, or is a radical of formula

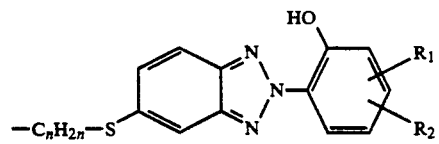

wherein n is 0 to 8, and $R_1$ and $R_2$ have the given meanings.

2. Photographic film material according to claim 1, wherein $R_1$ is hydrogen, alkyl of 1 to 18 carbon atoms, cyclohexyl, benzyl or cumyl, $R_2$ is alkyl of 1 to 18 carbon atoms, cyclohexyl, benzyl, cumyl or —CH₂CH₂CO₂R₆, wherein R₆ has the given meaning, and $R_3$ is phenyl or a radical of formula

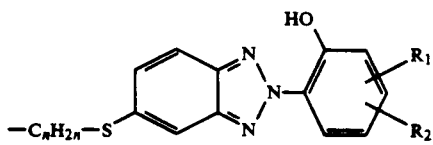

wherein n and $R_1$ and $R_2$ have the given meanings.

3. Photographic film material according to claim 1, wherein $R_1$ is hydrogen, alkyl of 1 to 18 carbon atoms, cyclohexyl, benzyl or cumyl, $R_2$ is alkyl of 1 to 18 carbon atoms, cyclohexyl, benzyl, cumyl or $-CH_2CH_2CO_2R_6$, wherein $R_6$ is alkyl of 6 to 12 carbon atoms, and $R_3$ is phenyl.

4. Photographic film material according to claim 3, wherein $R_1$ is hydrogen or tert-butyl, $R_2$ is methyl, tert-butyl, $-CH_2CH_2CO_2C_8H_{17}$ or $-CH_2CH_2CO_2C^*_8H_{17}$ ($C^*_8H_{17}$: mixture of octyl isomers) and $R_3$ is phenyl.

5. Photographic material according to claim 1, wherein the UV absorber of formula (1) is present in the substrate or in a layer above and/or under the substrate.

6. Photographic material according to claim 1, wherein the UV absorber of formula (1) is present in a light-sensitive layer.

7. Photographic material according to claim 1, wherein the UV absorber of formula (1) is present in a light-insensitive layer.

8. Photographic film material according to claim 1, wherein the UV absorber of formula (1) is present in an interlayer, a filter layer or a protective layer.

9. Photographic material according to claim 1, wherein the UV absorber of formula (1) is present in conjunction with UV absorbers of the type of the 2-hydroxyphenyltriazines, 2-hydroxybenzophenones and/or oxanilides.

10. A process for the reduction of static marks during the production of a photographic film material, which comprises incorporating a UV absorber of formula (1) according to claim 1 in the transparent substrate of said material or in a layer above and/or under the substrate.

11. A process for reducing fogging during the exposure of a photographic film material, which comprises incorporating a UV absorber of formula (1) according to claim 1 in the silver halide emulsion layer or layers.

* * * * *